Figure 1:
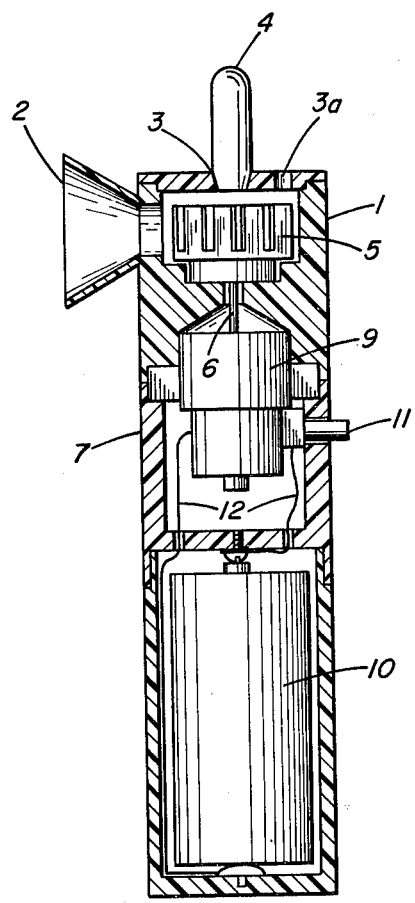

United States Patent [19]
Hansen

[11] 4,147,166
[45] Apr. 3, 1979

[54] ORAL INHALATOR POWDER DISPENSER

[75] Inventor: Lloyd F. Hansen, Campbell Hall, N.Y.

[73] Assignee: American Cyanamid Company, Stamford, Conn.

[21] Appl. No.: 792,748

[22] Filed: May 2, 1977

[51] Int. Cl.² ............................................. A61M 15/00
[52] U.S. Cl. .................................... 128/266; 128/208; 222/193
[58] Field of Search .............. 128/266, 265, 208, 206, 128/173 R, 173 H, 185, 187, 188, 203, 145.8, 145.6, 145 R, 142.3; 46/69; 222/193

[56] References Cited

U.S. PATENT DOCUMENTS

| | | | |
|---|---|---|---|
| 1,464,799 | 8/1923 | Anderson | 128/266 |
| 2,187,376 | 1/1940 | Guibert | 222/193 |
| 2,245,936 | 6/1941 | Nicholas | 46/69 R |
| 3,794,026 | 2/1974 | Jacobs | 128/145.8 |
| 3,831,606 | 8/1974 | Damani | 128/266 |
| 3,948,264 | 4/1976 | Wilke et al. | 128/266 |
| 3,971,377 | 7/1976 | Damani | 128/266 |
| 3,998,226 | 12/1976 | Harris | 128/266 |

Primary Examiner—Henry J. Recla
Attorney, Agent, or Firm—Charles F. Costello, Jr.

[57] ABSTRACT

A powder dispenser for inhalating a medicament which comprises a housing containing a converging funnel-shaped mouthpiece; an angular opening on the top of the housing to support a medicament capsule; an impeller; a shaft connected to the impeller at one end; and to a power source at the other end for driving the impeller.

The power source can be a battery driven motor, a compressed gas driven power turbine, or a hand power driven differential gear.

7 Claims, 3 Drawing Figures

ORAL INHALATOR POWDER DISPENSER

BACKGROUND OF THE INVENTION

This invention relates to a device intended for use as a pocket or portable unit for the use in oral inhalation therapy and to a process for using the device.

Currently, available devices for oral inhalation therapy employ halogenated hydrocarbons such as dichlorodifluoromethane as a propellent. Such propellents, for example, Freon ®, a registered trademark, are under scrutiny by various agencies of the federal government because of possible deleterious effects on the human body and on the environment. The dispenser of the present invention excludes the administration of halogenated hydrocarbons from the lung and from the environment during use.

U.S. Pat. No. 3,219,533 discloses many solid medicaments, including such steroids as hydrocortisone, prednisolone and dexamethasone dispersed in the particle size range of 0.5 to 10 microns in certain chlorofluoro alkanes using 0.5 to 5.0% ethanol, for inhalation and opthalmic therapy. U.S. Pat. No. 3,888,253 discloses a device for the administration of solid medicaments which uses the intake of breath as the means of power. Other patents, for example, U.S. Pat. No. 3,831,606 discloses means for atomizing the medicament. The present invention is an improvement over the device shown in U.S. Pat. No 3,831,606. Because the medicament capsule of the present invention is opened before being placed in the dispenser, more powder can be available for inhalation. That is, as contrasted to shattering in the dispenser, there is the possibility of complete use of all the powder from the medicament capsule by the use opening the capsule before inserting into the dispenser. Further, the atomizing means and the blower are combined into one impeller. There should thus be less powder loss because of the reduced surface area. Still further, the power source of the present invention is separated from the powder dispenser housing by a baffle or by a separate housing. Finally, the power source of the present invention may, but does not have to be, a battery driven motor. Still, other patents e.g., U.S. Pat. No. 3,948,264 discloses devices which use a vibration means and an intake of breath to administer a solid medicament. The patents discussed above are incorporated herein by reference.

What has been lacking in the prior art is a dispenser which will accurately dispense a certain amount of medicament, at a given velocity, and a given particle size. The nonhalogenated hydrocarbon devices heretofore have not in general provided this.

The discovery has now been made that an impeller contained in a housing which is attached to a converging funnel-shaped mouthpiece provides an accurate degree of atomization for medicament powders of different weight, powder density, and particle size. The type of impeller and the convergence of the funnel-shaped mouthpiece can be changed to accommodate medicament powders with different weight, powder density, and particle size. The advantages of the impeller in accurately atomizing and blowing the medicated powder into the mouthpiece lies in the fact that the impeller slings the powder in an arked path by centrifugal force out of the circular housing. The impeller thus provides a most accurate method of administering a prescribed dosage of medicated powder into the mouth and bronchial tree by inhalation.

In the event the federal government bans the use of halogenated hydrocarbon propellant devices, this dispenser can be a replacement as a accurate metered dose can be delivered without Freon ® or other halogenated hydrocarbons.

Because the power source of the oral inhalator powder dispenser does not need to be propelled by a halogenated hydrocarbon gas, the potential environmental pollution of the ozone layer of the earth can be minimized by the use of this dispenser. Of equal importance is the fact that this dispenser utilizes air as the medium for aerating the powder medicament. Therefore, the inhalator does not subject the user to any foreign gaseous substance with the use of this dispenser.

SUMMARY OF THE INVENTION

The oral inhalator powder dispenser of this invention consists of two principal parts. One part consists of a housing containing a converging funnel-shaped mouthpiece, a support for a medicament capsule, and an impellor. The other part consists of a power source to drive the impeller.

The power source is separated from the dispenser housing by a baffle, or in the alternative, is contained in a separate housing. A shaft connects the power source to the impeller. The impeller generates air turbulance which draws in the contents of a premeasured powder dose and discharges said powder into a body cavity, e.g., the mouth or bronchial tree.

The housing containing the funnel-shaped mouthpiece, the support for the medicament capsule, and the impeller can be any shape which allows for an efficient use of the impeller to impart centrifugal force to the powder and to thus carry the powder to the mouthpiece opening. In the preferred embodiment, the housing should be circular as this will allow for an equal arc around the circumference of the impeller. any shape which allows a complete dispensing of the powder from the medicament capsule into a body cavity in the user. Because in the preferred embodiment this dispenser is used orally, the size of the mouthpiece opening should be, at a maximum, smaller than the average mouth of a human being.

In the most preferred embodiment the converging funnel-shaped mouthpiece will be conical. The advantages of this shape are that it can easily fit into or near the mouth of the user easily. Also, the conical shape allows for the most uniform distribution of the aerated powder.

The support for the medicament capsule can be a box, clamp, clip, spring, or other means for holding the inverted capsule onto the housing containing the mouthpiece and impeller. In the preferred embodiment, the support for the medicament capsule would be an angular opening in the housing into which the capsule could fit securely without falling into the housing. In the most preferred embodiment this angular opening is such that the medicament capsule compresses slightly when the capsule is pushed by hand pressure into the opening. Thus, a snug fit will result. Adjacent the support means is one or a series of holes or rectangular openings in a concentric arrangement. The holes or openings allow the inlet of air which mixes with the medicament when the impeller is rotated.

A screen or sieve for use as a filter may be used with the support means. When used, the screen or sieve can also partially hold the powder in the inverted capsule from falling onto the impeller. It is to be understood, however, that this screen or sieve or other arresting means is not necessary to the practice of this invention. Because of the design of the dispenser housing, impeller, and mouthpiece of this invention, the powder from the medicament capsule will be evenly distributed by centrifugal force when the power source is energized. The support for the medicament capsule is approximately centered on the impeller. Thus, the powder is deposited onto or around the impeller equally. A sufficient and uniform atomization of the powder by the force of the impeller subsequently occurs.

Where the medicament powders used have a large particle size or heavy density, it may be necessary to tap the top of the inverted capsule initially to start the flow of the powder into the housing.

The impeller used with this invention can be any size or blade type, with any number of blades which supplies the proper centrifugal force to propel the medicament powder in an arc around the dispenser housing and out the funnel-shaped mouthpiece. For most medicament powders, a backward bladed or radial bladed impeller can be used. For other medicament powders, a combination of the backward and radial bladed impeller can be used.

The dispenser housing may be separate from or connected to the power source housing. Where the dispenser and power source are connected, a baffle separates the two parts. Both of these embodiments are preferred. In both embodiments, a shaft connects the impeller of the housing to the power source.

The power source may be any form of energy which will provide a continuous and constant velocity to the impeller. In one preferred embodiment, the power source is an electric motor. To energize the motor, a switch is provided between the batteries and the motor. The motor switch and batteries are contained in a housing.

In another preferred embodiment, a compressed gas container is attached through a standard valve to a power turbine chamber containing a power turbine. The turbine is connected by a shaft to the impeller. The inlet and exhaust ports for the compressed gas are separated from the converging funnel-shaped mouthpiece for the powder dispenser. Therefore, no compressed gas would enter the mouth and bronchial tree of the user. Because it appears to be commercially available and because, in most instances, it has a non-polluting effect on the environment, carbon dioxide as the compressed gas is preferred. However, other gases such as nitrous oxide and nitrogen may be used and are also preferred.

In another embodiment, the impeller shaft can be driven by a differential gear generated by hand power. This embodiment is the least effective because the amount of handpower delivered via a differential gear system to the impeller will not be uniform. Therefore, the amount of centrifugal force developed by the impeller will not be uniform. For this reason, a handheld power source is the least preferred for the purposes of this invention. It should be noted, however, that the handheld power source has advantages over the intake of breath by the user as the power source. As a general rule, a user in need of an oral inhalator powder dispenser does not have the lung capacity or strength to generate a sufficient breath to inhale a therapeutic amount of powder from the dispenser.

In yet another embodiment, the impeller shaft can be driven by a spiral band spring which is energized by a key or crank connected to the spring by ratchet means. When the ratchet plug is removed, the shaft is energized by the spring.

BRIEF DESCRIPTION OF THE DRAWINGS

FIG. 1 is a sideview of a preferred embodiment of this invention wherein the power source is electrically generated.

FIG. 2 is a sideview of another preferred embodiment of this invention wherein the power source is a compressed gas container which generates a power turbine.

FIG. 3 is a sideview of the power source of an embodiment of this invention wherein the power source is generated by hand through a differential gear system.

DETAILED DESCRIPTION OF THE INVENTION

There are two parts to the dispenser of this invention. One part is the dispenser unit. The other part is the power source. The dispenser unit is used the same way with any source of power. A capsule containing a medicament is separated and the longest half is inverted and inserted into the top of the dispenser unit. To avoid spillage of the medicament, the dispenser unit may alternatively be inverted before the capsule is inserted. When the dispenser is energized by the power source, air turbulance and vibration will dislodge the powder into the dispenser housing and subsequently into the air stream of the user.

The dispenser described in FIG. 1 employs a battery driven impeller as a means of supplying a high air volume at low pressure.

The dispenser described in FIG. 2 is of the same type, but differs in that a dual power turbine and impeller and a different energy source are used. One turbine is activated by compressed gas such as carbon dioxide or nitrogen. The power turbine is connected to an impeller which dislodges and mixes the powder to be inhalated by the user. The speed and air volume of the power turbine are controlled by the pressure supplied by the compressed gas.

Referring to FIG. 1, the powder dispenser housing 1 contains the converging funnel-shaped mouthpiece 2 and the support means for a medicament capsule 3. When an inverted capsule 4 is inserted into the support means 3 and the impeller 5 is rotated at a predetermined velocity by a power source transmitted by shaft 6, a metered dose of medicament can be administered into the mouth and bronchial tree of the user. Adjacent the support means is one hole or recess **3*a***. The hole or recess allows the inlet of air into the chamber which mixes with the medicament when the impeller is rotated. It is to be understood that a series of holes or rectangular openings in a concentric arrangement around the support means is also effective in allowing the inlet of air to the chamber. Therefore, the concentric arrangement of holes or openings is also preferred.

The power source may be contained in a housing 7. The bottom of housing 1 and the top of housing 7 are of sufficient thickness to act as a bearing surface for the shaft 6. Alternatively, as in FIG. 2 the unit for the powder dispenser housing and the power source housing can be connected. A baffle 8 is then required to separate the two parts and to maintain a proper vacuum in the impeller. The baffle 8 is of sufficient thickness to act as a bearing surface for the shaft 6. Referring again to FIG. 1, an electric motor 9 is connected to shaft 6. With a battery 10, energized by a switch 11 and transmitted by a wire 12, the electric motor 9 is of such voltage that a predetermined rotational velocity is imparted to shaft 6.

Figure 2:
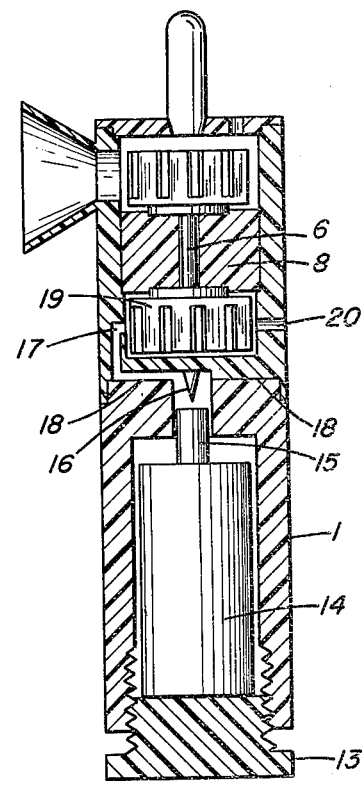

Viewing FIG. 2, the dispenser unit is as described above. A baffle 8 separates the impeller 5 in the powder dispenser housing 1 from the power turbine 19. The baffle 8 is of sufficient thickness to act as a bearing surface for the shaft 6. The housing 1 in this preferred embodiment contains both the dispenser unit and the power source. it is to be understood, however, that the housing may be as disclosed in FIG. 1, wherein the power source is contained in a separate housing 7. Also, in FIG. 2, housing 1 is shown with an end cap 13. It is to be understood that this end cap may be present but is not necessary to practice this invention.

The power source disclosed in FIG. 2 is a compressed gas container 14. The power source is generated by a valve means eg., a gate valve 15 on container 14 which is inserted into pin 16, or an aerosol valve. The gas stream then enters the gas inlet port 17 and into the power turbine chamber. The power turbine chamber is defined by baffles 8 and 18 and by the sidewalls of the housing 1. The gas stream imparts power to the power turbine 19, and is then exhausted from the exhaust port 20.

The pressure in the compressed gas container 14, the size of the opening in the inlet port 17, the size and number of the blades and the design of the power turbine 19, and the opening of the exhaust port 20, can be used in whole or in part to impart the desired rotational velocity to the shaft 6.

Figure 3:
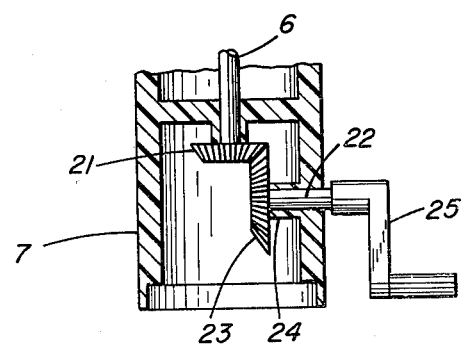

The drawing in FIG. 3 discloses an embodiment wherein the power source is generated by hand. As in FIG. 1, the power source in FIG. 3 is contained in housing 7 and is separate from the powder dispenser housing 1. The bottom of the housing 1 and the top of the housing 7 are of sufficient thickness to act as a bearing surface for the shaft 6. It is to be understood, however, that the housing in this embodiment may be as described in FIG. 2, wherein the dispenser unit and the power source are contained in a housing 1 separated by a baffle 8. The baffle 8 is of sufficient thickness to act as a bearing surface for the shaft 6.

Referring again to FIG. 3, a gear 21 is connected to the end of shaft 6. A gear 23 is connected to one end of a shaft 22 having a crank 25 at the other end for supplying the hand power. A bushing 24 stabilizes the shaft 22 as it passes through the housing 7 and is of sufficient thickness to act as a bearing surface for the shaft 22. The selection of gears 21 and 23 is such that a mechanical advantage is provided to the shaft 6 and subsequently to the impeller 5 when the crank 25 on shaft 22 is rotated.

I claim:

1. An oral inhalator powder dispenser comprising:
   (A) a cylindrical housing containing an upper and a lower portion; a baffle within said housing separating the upper and the lower portion; a converging funnel-shaped mouthpiece extending laterally from said upper portion; and communicating therewith; aperture means for supporting an open-ended powder medicament capsule on the top of said housing; an opening adjacent said aperture means on the top of said housing; an impeller disposed in said upper portion; and a shaft connected to said impeller at one end and protruding through said baffle; and
   (B) rotary means contained in the lower portion of said housing and connected to said shaft at the other end thereof.

2. A dispenser described in claim 1 wherein said aperture means is an angular opening on the top of said housing.

3. A dispenser described in claim 2 wherein said opening is in a concentric arrangement around said aperture means.

4. A dispenser described in claim 1 wherein said rotary means comprises:
   an electric motor connected to said shaft contained in the lower portion of said housing; at least one battery contained in the lower portion; a switch on the side of the lower portion; and an electric connecting means such that when said switch is activated, said motor will energize said shaft.

5. A dispenser described in claim 1 wherein said impeller is a backward bladed impeller.

6. A dispenser described in claim 1 wherein said impeller is a radial bladed impeller.

7. An oral inhalator powder dispenser comprising:
   (A) a cylindrical housing containing an upper and a lower portion; an impeller disposed in the top section of said upper portion; a power turbine disposed in the bottom of said upper portion; a first baffle within said housing separating said impeller in the top and extending laterally from said power turbine in the bottom of the upper portion and a second baffle separating the upper and the lower portion; a converging funnel-shaped mouthpiece on the side of the upper portion; and communicating therewith; aperture means for supporting an open-ended powder medicament capsule on the top of said housing; an opening adjacent said aperture means on the top of said housing; a shaft connected to said impeller at one end and protruding through said first baffle and connected to said power turbine at the other end thereof; and a
   (B) Compressed gas power source contained in the lower portion of said housing wherein said power source comprises: a compressed gas container having an outlet portion and a valve in said outlet portion; said bottom of said upper portion defining a chamber within which said turbine is rotably disposed; said chamber having an an inlet port and an exhaust port opposingly disposed in said housing adjacent said power turbine, said inlet port extending through said second baffle and connected to said outlet portion of said container, and said outlet port communicating to atmosphere; a pin secured in said gas inlet port adjacent said outlet portion of said container; and means in said lower portion for activating said gas container valve by said pin whereby, the compressed gas will rotate said power turbine and energize said shaft.

* * * * *